United States Patent [19]
Donaldson et al.

[11] Patent Number: 6,057,128
[45] Date of Patent: May 2, 2000

[54] MU-1, MEMBER OF THE CYTOKINE RECEPTOR FAMILY

[75] Inventors: Debra D. Donaldson, Medford; Michelle Unger, Somerville, both of Mass.

[73] Assignee: Genetics Institute, Inc., Cambridge, Mass.

[21] Appl. No.: 09/040,005

[22] Filed: Mar. 17, 1998

[51] Int. Cl.⁷ ............................. C12N 15/12; C12N 15/62

[52] U.S. Cl. .................... 435/69.1; 435/69.7; 435/252.3; 435/320.1; 536/23.4; 536/23.5

[58] Field of Search .................................. 435/69.1, 69.7, 435/252.3, 320.1; 530/350; 536/23.4, 23.5

[56] References Cited

PUBLICATIONS

Hatakeyama et al. Interleukin–2 Receptor beta Chain Gene: Generation of Three Receptor Forms by Cloned Human alpha and beta Chain cDNA's. Science 244:551–556, May 1989.

D'Andrea et al. Expression Cloning of the Murine Erythropoietin Receptor. Cell 57:277–285, May 1989.

*Primary Examiner*—John Ulm
*Attorney, Agent, or Firm*—Suzanne A. Sprunger; Scott A. Brown

[57] ABSTRACT

Polynucleotides encoding the MU-1 hematopoietin receptor superfamily chain and fragments thereof are disclosed. MU-1 proteins and methods for their production are also disclosed.

14 Claims, No Drawings

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 2665 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:1:

```
GTCGACTGGA GGCCCAGCTG CCCGTCATCA GAGTGACAGG TCTTATGACA GCCTGATTGG      60

TGACTCGGGC TGGGTGTGGA TTCTCACCCC AGGCCTCTGC CTGCTTTCTC AGACCCTCAT     120

CTGTCACCCC CACGCTGAAC CCAGCTGCCA CCCCCAGAAG CCCATCAGAC TGCCCCCAGC     180

ACACGGAATG GATTTCTGAG AAAGAAGCCG AAACAGAAGG CCCGTGGGAG TCAGCATGCC     240

GCGTGGCTGG GCCGCCCCCT TGCTCCTGCT GCTGCTCCAG GGAGGCTGGG GCTGCCCCGA     300

CCTCGTCTGC TACACCGATT ACCTCCAGAC GGTCATCTGC ATCCTGGAAA TGTGGAACCT     360

CCACCCCAGC ACGCTCACCC TTACCTGGCA AGACCAGTAT GAAGAGCTGA AGGACGAGGC     420

CACCTCCTGC AGCCTCCACA GGTCGGCCCA CAATGCCACG CATGCCACCT ACACCTGCCA     480

CATGGATGTA TTCCACTTCA TGGCCGACGA CATTTTCAGT GTCAACATCA CAGACCAGTC     540

TGGCAACTAC TCCCAGGAGT GTGGCAGCTT TCTCCTGGCT GAGAGCATCA AGCCGGCTCC     600

CCCTTTCAAC GTGACTGTGA CCTTCTCAGG ACAGTATAAT ATCTCCTGGC GCTCAGATTA     660

CGAAGACCCT GCCTTCTACA TGCTGAAGGG CAAGCTTCAG TATGAGCTGC AGTACAGGAA     720

CCGGGGAGAC CCCTGGGCTG TGAGTCCGAG GAGAAAGCTG ATCTCAGTGG ACTCAAGAAG     780
```

-continued

```
TGTCTCCCTC CTCCCCCTGG AGTTCCGCAA AGACTCGAGC TATGAGCTGC AGGTGCGGGC      840

AGGGCCCATG CCTGGCTCCT CCTACCAGGG GACCTGGAGT GAATGGAGTG ACCCGGTCAT      900

CTTTCAGACC CAGTCAGAGG AGTTAAAGGA AGGCTGGAAC CCTCACCTGC TGCTTCTCCT      960

CCTGCTTGTC ATAGTCTTCA TTCCTGCCTT CTGGAGCCTG AAGACCCATC CATTGTGGAG     1020

GCTATGGAAG AAGATATGGG CCGTCCCCAG CCCTGAGCGG TTCTTCATGC CCCTGTACAA     1080

GGGCTGCAGC GGAGACTTCA AGAAATGGGT GGGTGCACCC TTCACTGGCT CCAGCCTGGA     1140

GCTGGGACCC TGGAGCCCAG AGGTGCCCTC CACCCTGGAG GTGTACAGCT GCCACCCACC     1200

ACGGAGCCCG GCCAAGAGGC TGCAGCTCAC GGAGCTACAA GAACCAGCAG AGCTGGTGGA     1260

GTCTGACGGT GTGCCCAAGC CCAGCTTCTG GCCGACAGCC CAGAACTCGG GGGGCTCAGC     1320

TTACAGTGAG GAGAGGGATC GGCCATACGG CCTGGTGTCC ATTGACACAG TGACTGTGCT     1380

AGATGCAGAG GGGCCATGCA CCTGGCCCTG CAGCTGTGAG GATGACGGCT ACCCAGCCCT     1440

GGACCTGGAT GCTGGCCTGG AGCCCAGCCC AGGCCTAGAG GACCCACTCT GGATGCAGG     1500

GACCACAGTC CTGTCCTGTG GCTGTGTCTC AGCTGGCAGC CCTGGGCTAG AGGGCCCCT     1560

GGGAAGCCTC CTGGACAGAC TAAAGCCACC CCTTGCAGAT GGGGAGGACT GGGCTGGGGG     1620

ACTGCCCTGG GGTGGCCGGT CACCTGGAGG GGTCTCAGAG AGTGAGGCGG GCTCACCCCT     1680

GGCCGGCCTG GATATGGACA CGTTTGACAG TGGCTTTGTG GGCTCTGACT GCAGCAGCCC     1740

TGTGGAGTGT GACTTCACCA GCCCCGGGGA CGAAGGACCC CCCCGGAGCT ACCTCCGCCA     1800

GTGGGTGGTC ATTCCTCCGC CACTTTCGAG CCCTGGACCC CAGGCCAGCT AATGAGGCTG     1860

ACTGGATGTC CAGAGCTGGC CAGGCCACTG GGCCCTGAGC CAGAGACAAG GTCACCTGGG     1920

CTGTGATGTG AAGACACCTG CAGCCTTTGG TCTCCTGGAT GGGCCTTTGA GCCTGATGTT     1980

TACAGTGTCT GTGTGTGTGT GTGCATATGT GTGTGTGTGC ATATGCATGT GTGTGTGTGT     2040

GTGTGTCTTA GGTGCGCAGT GGCATGTCCA CGTGTGTGTG TGATTGCACG TGCCTGTGGG     2100

CCTGGGATAA TGCCCATGGT ACTCCATGCA TTCACCTGCC CTGTGCATGT CTGGACTCAC     2160

GGAGCTCACC CATGTGCACA AGTGTGCACA GTAAACGTGT TTGTGGTCAA CAGATGACAA     2220

CAGCCGTCCT CCCTCCTAGG GTCTTGTGTT GCAAGTTGGT CCACAGCATC TCCGGGGCTT     2280

TGTGGGATCA GGGCATTGCC TGTGACTGAG GCGGAGCCCA GCCCTCCAGC GTCTGCCTCC     2340

AGGAGCTGCA AGAAGTCCAT ATTGTTCCTT ATCACCTGCC AACAGGAAGC GAAAGGGGAT     2400

GGAGTGAGCC CATGGTGACC TCGGGAATGG CAATTTTTTG GGCGGCCCCT GGACGAAGGT     2460

CTGAATCCCG ACTCTGATAC CTTCTGGCTG TGCTACCTGA GCCAAGTCGC CTCCCCTCTC     2520

TGGGCTAGAG TTTCCTTATC CAGACAGTGG GGAAGGCATG ACACACCTGG GGGAAATTGG     2580

CGATGTCACC CGTGTACGGT ACGCAGCCCA GAGCAGACCC TCAATAAACG TCAGCTTCCT     2640

TCAAAAAAAA AAAAAAAAAT CTAGA                                          2665
```

(2) INFORMATION FOR SEQ ID NO:2:

(i) SEQUENCE CHARACTERISTICS:
        (A) LENGTH: 538 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

```
Met Pro Arg Gly Trp Ala Ala Pro Leu Leu Leu Leu Leu Gln Gly
1               5                   10                  15
```

-continued

```
Gly Trp Gly Cys Pro Asp Leu Val Cys Tyr Thr Asp Tyr Leu Gln Thr
             20                  25                  30

Val Ile Cys Ile Leu Glu Met Trp Asn Leu His Pro Ser Thr Leu Thr
         35                  40                  45

Leu Thr Trp Gln Asp Gln Tyr Glu Glu Leu Lys Asp Glu Ala Thr Ser
     50                  55                  60

Cys Ser Leu His Arg Ser Ala His Asn Ala Thr His Ala Thr Tyr Thr
 65                  70                  75                  80

Cys His Met Asp Val Phe His Phe Met Ala Asp Ile Phe Ser Val
                 85                  90                  95

Asn Ile Thr Asp Gln Ser Gly Asn Tyr Ser Gln Glu Cys Gly Ser Phe
                100                 105                 110

Leu Leu Ala Glu Ser Ile Lys Pro Ala Pro Pro Phe Asn Val Thr Val
            115                 120                 125

Thr Phe Ser Gly Gln Tyr Asn Ile Ser Trp Arg Ser Asp Tyr Glu Asp
        130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
        275                 280                 285

Lys Lys Trp Val Gly Ala Pro Phe Thr Gly Ser Ser Leu Glu Leu Gly
    290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
    370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430
```

```
Ala Gly Ser Pro Gly Leu Gly Gly Pro Leu Gly Ser Leu Leu Asp Arg
            435                 440                 445

Leu Lys Pro Pro Leu Ala Asp Gly Glu Asp Trp Ala Gly Gly Leu Pro
    450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
            515                 520                 525

Pro Leu Ser Ser Pro Gly Pro Gln Ala Ser
    530                 535
```

(2) INFORMATION FOR SEQ ID NO:3:

(i) SEQUENCE CHARACTERISTICS:
        (A) LENGTH: 70 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
Leu Met Thr Asn Ala Phe Ile Ser Ile Ile Asp Asp Leu Ser Lys Tyr
1               5                   10                  15

Asp Val Gln Val Arg Ala Ala Val Ser Ser Met Cys Arg Glu Ala Gly
                20                  25                  30

Leu Trp Ser Glu Trp Ser Gln Pro Ile Tyr Val Gly Asn Asp Glu His
            35                  40                  45

Lys Pro Leu Arg Glu Trp Phe Val Ile Val Ile Met Ala Thr Ile Cys
    50                  55                  60

Phe Ile Leu Leu Ile Leu
65              70
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:4:

GAGTCCGAGG AGAAAGCTGA TCTCA                                  25

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:5:

```
GAAAGATGAC CGGGTCACTC CATT                                                        24

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO:6:

ACTCGAGCTA TGAGCTGCAG GTGCGGGCA                                                   29

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO:7:

ACTCGAGCTA TGAGCTGCAG GTGCGGGCA                                                   29

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Trp Ser Xaa Trp Ser
1               5
```

MU-1, MEMBER OF THE CYTOKINE RECEPTOR FAMILY

FIELD OF THE INVENTION

The present invention relates to new members of the mammalian cytokine receptor family of proteins (including without limitation human and murine receptor proteins), fragments thereof and recombinant polynucleotides and cells useful for expressing such proteins.

BACKGROUND OF THE INVENTION

A variety of regulatory molecules, known as hematopoietins been identified which are involved in the development and proliferation of the various populations of hematopoietic or blood cells. Most hematopoietins exhibits certain biological activities by interacting with a receptor on the surface of target cells. Cytokine receptors are commonly composed of one, two or three chains. Many cytokine receptors and some cytokines, such as IL-12 p40, are members of the hematopoietin receptor superfamily of proteins. Identification of new members of the hematopoietin receptor superfamily can be useful in regulation of hematopoiesis, in regulation of immune responses and in identification of other members of the hematopoietin superfamily, including cytokines and receptors.

It would be desirable to identify and determine the DNA and protein sequence for heretofore unknown members of the hematopoietin receptor superfamily.

SUMMARY OF THE INVENTION

In accordance with the present invention, polynucleotides encoding the MU-1 hematopoietin receptor superfamily chain are disclosed, including without limitation those from the murine and human sources.

In certain embodiments, the invention provides an isolated polynucleotide comprising a nucleotide sequence selected from the group consisting of:

(a) the nucleotide sequence of SEQ ID NO:1;
(b) the nucleotide sequence of SEQ ID NO:1 from nucleotide 238 to nucleotide 1852;
(c) the nucleotide sequence of SEQ ID NO:1 from nucleotide 301 to nucleotide 1852;
(d) the nucleotide sequence of SEQ ID NO:1 from nucleotide 301 to nucleotide 945;
(e) a nucleotide sequence varying from the sequence of the nucleotide sequence specified in any of (a)–(d) as a result of degeneracy of the genetic code;
(f) a nucleotide sequence capable of hybridizing under stringent conditions to the nucleotide specified in any of (a)–(d);
(g) a nucleotide sequence encoding a species homologue of the sequence of SEQ ID NO:2; and
(h) an allelic variant of the nucleotide sequence specified in any of (a)–(d).

Preferably, the nucleotide sequence encodes a protein having a biological activity of the MU-1 hematopoietin receptor superfamily chain. The nucleotide sequence may be operably linked to an expression control sequence.

The invention also provides isolated polynucleotides comprising a nucleotide sequence encoding a peptide or protein comprising an amino acid sequence selected from the group consisting of:

(a) the amino acid sequence of SEQ ID NO:2;
(b) the amino acid sequence of SEQ ID NO:2 from amino acids 22 to 538;
(c) the amino acid sequence of SEQ ID NO:2 from amino acids 22 to 236;
(d) the amino acid sequence of SEQ ID NO:2 from amino acids 1 to 236; and
(e) fragments of (a)–(d) having a biological activity of the MU-1 hematopoietin receptor superfamily chain.

Host cells, preferably mammalian cells, transformed with the polynucleotides are also provided.

In other embodiments, the invention provides a process for producing a MU-1 protein. The process comprises:

(a) growing a culture of the host cell of the present invention in a suitable culture medium; and
(b) purifying the human MU-1 protein from the culture.

Proteins produced according to these methods are also provided.

The present invention also provides for an isolated MU-1 protein comprising an amino acid sequence selected from the group consisting of:

(a) the amino acid sequence of SEQ ID NO:2;
(b) the amino acid sequence of SEQ ID NO:2 from amino acids 22 to 538;
(c) the amino acid sequence of SEQ ID NO:2 from amino acids 22 to 236;
(d) the amino acid sequence of SEQ ID NO:2 from amino acids 1 to 236; and
(e) fragments of (a)–(d) having a biological activity of the MU-1 hematopoietin receptor superfamily chain. In other preferred embodiments, the specified amino acid sequence is part of a fusion protein (with an additional amino acid sequence not derived from MU-1).

Preferred fusion proteins comprise an antibody fragment, such as an Fc fragment.

Pharmaceutical compositions comprising a protein of the present invention and a pharmaceutically acceptable carrier are also provided.

The present invention further provides for compositions comprising an antibody which specifically reacts with a protein of the present invention.

DETAILED DESCRIPTION OF PREFERRED EMBODIMENTS

The inventors of the present application have for the first time identified and provided polynucleotides encoding the MU-1 hematopoietin receptor superfamily chain (hereinafter "MU-1" or "MU-1 protein"), including without limitation polynucleotides encoding human MU-1.

A 70 amino acid region of the human IL5 receptor (LMTNAFISIIDDLSKYDVQVRAAVSSMCREAGLWS EWSQPIYVGNDEHKPLREWFVIVIMATICFILLIL, SEQ ID NO:3) was used to search the GenBank EST database using the TBLASTN algorithm. Sequence within the genomic BAC clone AC002303 from human chromosome 16p12 was identified with homology to this region, suggesting that this segment might encode a gene for a novel hematopoietin receptor. Examination of open reading frames within 1000 bp of nucleotide 40,886 revealed a 270 bp open frame which when used in a BLASTP search of GenPept exclusively identified members of the cytokine receptor family. A stop codon present at the end of this reading frame was interpreted as indication of transition over an exon/intron border.

It was then determined whether RNA was transcribed from a gene contained within this BAC clone from chromosome 16p12. PCR primers were synthesized based on the largest ORF segment which contained peptide sequence conserved within the cytokine receptor family. Primers GAGTCCGAGGAGAAAGCTGATCTCA (5p) (SEQ ID NO:4) and GAAAGATGACCGGGTCACTCCATT (3p) (SEQ ID NO:5) were used in PCRs to screen phage libraries from various human tissues (Clontech). PCR products of the expected 164 bp size which specifically hybridized to a 32-P labeled oligonucleotide of the sequence ACTCGAGCTAT-GAGCTGCAGGTGCGGGCA (SEQ ID NO:6) were observed in phage from lung, kidney, placenta and heart. Using the oligonucleotide ACTCGAGCTATGAGCTG-CAGGTGCGGGCA (SEQ ID NO:7) a full-length cDNA clone NN14-1b (MU-1) was identified, purified, and sequenced. The DNA sequence and the predicted amino acid sequence are shown in SEQ ID NO:1 and SEQ ID NO:2, respectively. The open reading frame encodes a novel member of the hematopoietin receptor family. It has a leader sequence, conserved cysteine pairs, PP, and WSXWS (SEQ ID NO:8) motifs characteristic of the family as well as a transmembrane domain and extensive cytoplasmic domain. Subsequent FASTA alignment of this sequence with Gen-Pept showed greatest homology with human IL-2Rb. The predicted amino acid sequence of the receptor chain includes a putative signal sequence from amino acids 1–21. The mature human MU-1 is believed to have the sequence of amino acids 24–538 of SEQ ID NO:2. A transmembrane domain is found at amino acids 237–254.

The MU-1 cDNA was deposited with the American Type Culture Collection on Mar. 10, 1998, as accession number ATCC 98687.

Any forms of MU-1 proteins of less than full length are encompassed within the present invention and are referred to herein collectively with full length and mature forms as "MU-1" or "MU-1 proteins." MU-1 proteins of less than full length may be produced by expressing a corresponding fragment of the polynucleotide encoding the full-length MU-1 protein (SEQ ID NO:4 or SEQ ID NO:6). These corresponding polynucleotide fragments are also part of the present invention. Modified polynucleotides as described above may be made by standard molecular biology techniques, including construction of appropriate desired deletion mutants, site-directed mutagenesis methods or by the polymerase chain reaction using appropriate oligonucleotide primers.

For the purposes of the present invention, a protein has "a biological activity of the MU-1 hematopoietin receptor superfamily chain" if it possess one or more of the biological activities of the corresponding mature MU-1 protein.

MU-1 or active fragments thereof (MU-1 proteins) may be fused to carrier molecules such as immunoglobulins. For example, soluble forms of the MU-1 may be fused through "linker" sequences to the Fc portion of an immunoglobulin. Other fusions proteins, such as those with GST, Lex-A or MBP, may also be used.

The invention also encompasses allelic variants of the nucleotide sequence as set forth in SEQ ID NO:1, that is, naturally-occurring alternative forms of the isolated polynucleotide of SEQ ID NO:1 which also encode MU-1 proteins, preferably those proteins having a biological activity of MU-1. Also included in the invention are isolated polynucleotides which hybridize to the nucleotide sequence set forth in SEQ ID NO:1 under highly stringent conditions (for example, 0.1×SSC at 65° C.). Isolated polynucleotides which encode MU-1 proteins but which differ from the nucleotide sequence set forth in SEQ ID NO:1 by virtue of the degeneracy of the genetic code are also encompassed by the present invention. Variations in the nucleotide sequence as set forth in SEQ ID NO:1 which are caused by point mutations or by induced modifications are also included in the invention.

The present invention also provides polynucleotides encoding homologues of the human MU-1 from other animal species, particularly other mammalian species. Species homologues can be identified and isolated by making probes or primers from the murine or human sequences disclosed herein and screening a library from an appropriate species, such as for example libraries constructed from PBMCs, thymus or testis of the relevant species.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the MU-1 protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the MU-1 protein is expressed by a host cell which has been transformed (transfected) with the ligated polynucleotide/expression control sequence.

A number of types of cells may act as suitable host cells for expression of the MU-1 protein. Any cell type capable of expressing functional MU-1 protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12, M1x or C2C12 cells.

The MU-1 protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif. U.S.A. (the MaxBac® kit), and such methods are well known in the art, as described in Summers and Smith, *Texas Agricultural Experiment Station Bulletin No.* 1555 (1987), incorporated herein by reference. Soluble forms of the MU-1 protein may also be produced in insect cells using appropriate isolated polynucleotides as described above.

Alternatively, the MU-1 protein may be produced in lower eukaryotes such as yeast or in prokaryotes such as bacteria. Suitable yeast strains include Saccharomyces cerevisiae, Schizosaccharomyces pombe, Kluyveromyces strains, Candida, or any yeast strain capable of expressing heterologous proteins. Suitable bacterial strains include *Escherichia coli, Bacillus subtilis, Salmonella typhimurium,* or any bacterial strain capable of expressing heterologous proteins.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment which allows correct formation of disulfide bonds (a redox system). General methods of refolding are disclosed in Kohno, *Meth. Enzym.*, 185:187–195 (1990). EP 0433225 and copending application U.S. Ser. No. 08/163,877 describe other appropriate methods.

The MU-1 protein of the invention may also be expressed as a product of transgenic animals, e.g., as a component of the milk of transgenic cows, goats, pigs, or sheep which are characterized by somatic or germ cells containing a polynucleotide sequence encoding the MU-1 protein.

The MU-1 protein of the invention may be prepared by growing a culture transformed host cells under culture conditions necessary to express the desired protein. The resulting expressed protein may then be purified from the culture medium or cell extracts. Soluble forms of the MU-1 protein of the invention can be purified from conditioned media. Membrane-bound forms of MU-1 protein of the invention can be purified by preparing a total membrane fraction from the expressing cell and extracting the membranes with a non-ionic detergent such as Triton X-100.

The MU-1 protein can be purified using methods known to those skilled in the art. For example, the MU-1 protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the MU-1 protein from culture supernatant may also include one or more column steps over such affinity resins as concanavalin A-agarose, heparintoyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the MU-1 protein. Affinity columns including antibodies to the MU-1 protein can also be used in purification in accordance with known methods. Some or all of the foregoing purification steps, in various combinations or with other known methods, can also be employed to provide a substantially purified isolated recombinant protein. Preferably, the isolated MU-1 protein is purified so that it is substantially free of other mammalian proteins.

MU-1 proteins of the invention may also be used to screen for agents which are capable of binding to MU-1. Binding assays using a desired binding protein, immobilized or not, are well known in the art and may be used for this purpose using the MU-1 protein of the invention. Purified cell based or protein based (cell free) screening assays may be used to identify such agents. For example, MU-1 protein may be immobilized in purified form on a carrier and binding or potential ligands to purified MU-1 protein may be measured.

MU-1 proteins, purified from cells or recombinantly produced, may be used as a pharmaceutical composition when combined with a pharmaceutically acceptable carrier. Such a composition may contain, in addition to MU-1 or inhibitor and carrier, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-14, IL-15, G-CSF, stem cell factor, and erythropoietin. The pharmaceutical composition may also include anti-cytokine antibodies. The pharmaceutical composition may contain thrombolytic or anti-thrombotic factors such as plasminogen activator and Factor VIII. The pharmaceutical composition may further contain other anti-inflammatory agents. Such additional factors and/or agents may be included in the pharmaceutical composition to produce a synergistic effect with isolated MU-1 protein, or to minimize side effects caused by the isolated MU-1 protein. Conversely, isolated MU-1 protein may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated MU-1 protein is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated MU-1 protein is administered to a mammal. Isolated MU-1 protein may be administered in accordance with the method of the invention either alone or in combination with other therapies such as treatments employing cytokines, lymphokines or other hematopoietic factors. When co-administered with one or more cytokines, lymphokines or other hematopoietic factors, MU-1 protein may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering MU-1 protein in combination with cytokine (s), lymphokine(s), other hematopoietic factor(s), thrombolytic or anti-thrombotic factors.

Administration of MU-1 protein used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of MU-1 protein is administered orally, MU-1 protein will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% MU-1 protein, and preferably from about 25 to 90% MU-1 protein. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of MU-1 protein, and preferably from about 1 to 50% MU-1 protein.

When a therapeutically effective amount of MU-1 protein is administered by intravenous, cutaneous or subcutaneous injection, MU-1 protein will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to MU-1 protein an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of MU-1 protein in the pharmaceutical composition of the present invention will depend upon the nature and severity of the condition being treated, and on the nature of prior treatments which the patient has undergone. Ultimately, the attending physician will decide the amount of MU-1 protein with which to treat each individual patient. Initially, the attending physician will administer low doses of MU-1 protein and observe the patient's response. Larger doses of MU-1 protein may be administered until the optimal therapeutic effect is obtained for the patient, and at that point the dosage is not generally increased further. It is contemplated that the various pharmaceutical compositions used to practice the method of the present invention should contain about 0.1 $\mu$g to about 100 mg of MU-1 protein per kg body weight.

The duration of intravenous therapy using the pharmaceutical composition of the present invention will vary, depending on the severity of the disease being treated and the condition and potential idiosyncratic response of each individual patient. It is contemplated that the duration of each application of the MU-1 protein will be in the range of 12 to 24 hours of continuous intravenous administration. Ultimately the attending physician will decide on the appropriate duration of intravenous therapy using the pharmaceutical composition of the present invention.

The polynucleotide and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology*. J. E.e.a. Coligan eds. Vol 1 pp. 3.12.1–3.12.14, John Wiley and Sons, Toronto. 1994; and Measurement of mouse and human Interferon $\gamma$, Schreiber, R. D. In *Current Protocols in Immunology*. J. E.e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J. E.e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In *Current Protocols in Immunology*. J. E.e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11—Bennett, F., Giannotti, J., Clark, S. C. and Turner, K. J. In *Current Protocols in Immunology.* J. E.e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In *Current Protocols in Immunology.* J. E.e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. U.S.A. 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

The MU-1 DNA also maps to the chromosomal locus for Crohn's disease. As a result, proteins of the present invention may be used to treat Crohn's disease and other inflammatory bowel diseases.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci U.S.A., 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process.

Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class α a chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. U.S.A. 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. U.S.A. 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowmanet al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E.e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. U.S.A. 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M.G. In *Culture of Hematopoietic Cells*. R. I. Freshney, et al. eds. Vol pp. 265–268, Wiley-Liss, Inc., New York, N.Y. 1994; Hirayama et al., Proc. Natl. Acad. Sci. U.S.A. 89:5907–5911, 1992; Primitive hematopoietic colony forming cells with high proliferative potential, McNiece, I. K. and Briddell, R. A. In *Culture of Hematopoietic Cells*. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells*. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163–179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139–162, Wiley-Liss, Inc., New York, N.Y. 1994.

Research Uses and Utilities

Polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

MU-1 proteins of the invention may also be used to immunize animals to obtain polyclonal and monoclonal antibodies which specifically react with the MU-1 protein and which may inhibit binding of ligands to the receptor. Such antibodies may be obtained using the entire MU-1 as an immunogen, or by using fragments of MU-1. Smaller fragments of the MU-1 may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J.Amer.Chem-.Soc. 85, 2149–2154 (1963); J. L. Krstenansky, et al., FEBS Lett. 211, 10 (1987).

Neutralizing or non-neutralizing antibodies (preferably monoclonal antibodies) binding to MU-1 protein may also be useful therapeutics for certain tumors and also in the treatment of conditions described above. These neutralizing monoclonal antibodies may be capable of blocking ligand binding to the MU-1 receptor chain.

All patent and literature references cited herein are incorporated by reference as if fully set forth.

What is claimed is:

1. An isolated polynucleotide comprising a nucleotide sequence selected from the group consisting of:
    (a) the nucleotide sequence of SEQ ID NO:1;
    (b) the nucleotide sequence of SEQ ID NO:1 from nucleotide 238 to nucleotide 1852;
    (c) the nucleotide sequence of SEQ ID NO:1 from nucleotide 301 to nucleotide 1852;
    (d) the nucleotide sequence of SEQ ID NO:1 from nucleotide 301 to nucleotide 945;
    (e) a nucleotide sequence encoding the protein encoded by (b) above in the reading frame beginning with nucleotide 238 and varying from the nucleotide sequence of (b) as a result of degeneracy of the genetic code;
    (f) a nucleotide sequence encoding the protein encoded by (c) above in the reading frame beginning with nucleotide 301 and varying from the nucleotide sequence of (c) as a result of degeneracy of the genetic code; and
    (g) a nucleotide sequence encoding the protein encoded by (d) above in the reading frame beginning with nucleotide 301 and varying from the nucleotide sequence of (d) as a result of degeneracy of the genetic code.

2. The polynucleotide of claim 1 wherein said nucleotide sequence is operably linked to an expression control sequence.

3. A host cell transformed with the polynucleotide of claim 2.

4. The host cell of claim 3, wherein said cell is a mammalian cell.

5. The polynucleotide of claim 1 comprising the nucleotide sequence of SEQ ID NO:1.

6. The polynucleotide of claim 1 comprising the nucleotide sequence of SEQ ID NO:1 from nucleotide 238 to nucleotide 1852.

7. A process for producing a protein, said process comprising:
    (a) growing a culture of a host cell in a suitable culture medium, wherein said host cell is transformed with a polynucleotide of claim 1 operably linked to an expression control sequence; and
    (b) purifying the protein encoded by said polynucleotide from the culture.

8. The polynucleotide of claim 1 comprising the nucleotide sequence of SEQ ID NO:1 from nucleotide 301 to nucleotide 1852.

9. The polynucleotide of claim 1 comprising the nucleotide sequence of SEQ ID NO:1 from nucleotide 238 to nucleotide 945.

10. An isolated polynucleotide comprising a nucleotide sequence encoding a peptide or protein comprising an amino acid sequence selected from the group consisting of:
 (a) the amino acid sequence of SEQ ID NO:2;
 (b) the amino acid sequence of SEQ ID NO:2 from amino acids 22 to 538;
 (c) the amino acid sequence of SEQ ID NO:2 from amino acids 22 to 236; and
 (d) the amino acid sequence of SEQ ID NO:2 from amino acids 1 to 236.

11. The polynucleotide of claim 10 which encodes a peptide or protein comprising the amino acid sequence of SEQ ID NO:2.

12. The polynucleotide of claim 10 which encodes a peptide or protein comprising the amino acid sequence of SEQ ID NO:2 from amino acid 22 to amino acid 538.

13. The polynucleotide of claim 10 which encodes a peptide or protein comprising the amino acid sequence of SEQ ID NO:2 from amino acid 22 to amino acid 236.

14. The polynucleotide of claim 10 which encodes a peptide of protein comprising the amino acid sequence of SEQ ID NO:2 from amino acid 1 to amino acid 236.

* * * * *